United States Patent
Wo et al.

(10) Patent No.: US 7,067,076 B2
(45) Date of Patent: Jun. 27, 2006

(54) FLAME RETARDANT PHOSPHONATE ADDITIVES FOR THERMOPLASTICS

(75) Inventors: Shiming Wo, Monroe Township, NJ (US); Dwight Shamblee, North Charleston, SC (US)

(73) Assignee: Rhodia Inc., Cranbury, NJ (US)

( * ) Notice: Subject to any disclaimer, the term of this patent is extended or adjusted under 35 U.S.C. 154(b) by 71 days.

(21) Appl. No.: 10/902,538

(22) Filed: Jul. 29, 2004

(65) Prior Publication Data

US 2005/0038144 A1    Feb. 17, 2005

Related U.S. Application Data

(60) Provisional application No. 60/491,914, filed on Aug. 1, 2003.

(51) Int. Cl.
  *C09K 21/12* (2006.01)
  *C07F 9/6571* (2006.01)
  *C07F 9/6574* (2006.01)
  *C08K 5/5337* (2006.01)

(52) U.S. Cl. .......... 252/609; 568/12; 568/14; 524/108; 524/117; 524/119; 524/127

(58) Field of Classification Search .......... 252/609
  See application file for complete search history.

(56) References Cited

U.S. PATENT DOCUMENTS 3,789,091 A * 1/1974 Anderson et al. .......... 558/77
3,849,368 A * 11/1974 Anderson et al. .......... 524/119
4,073,767 A * 2/1978 Birum .......... 524/118
4,397,759 A * 8/1983 Hancock .......... 252/609
5,126,387 A * 6/1992 Hand .......... 524/118
5,710,305 A * 1/1998 Archer et al. .......... 558/77
5,961,996 A * 10/1999 Garson et al. .......... 424/401
6,502,325 B1 * 1/2003 Zappone et al. .......... 34/357
6,576,700 B1   6/2003 Patel .......... 524/508

* cited by examiner

Primary Examiner—Joseph D. Anthony

(57) ABSTRACT

The invention is directed to a phosphonate composition having flame retardant properties. The phosphonate composition of the invention has the general formula:

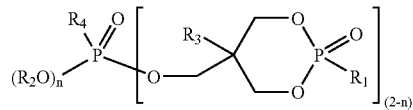

wherein
  $R_1$ and $R_2$ are independently $C_1$–$C_4$ alkyl,
  $R_3$ is H or $C_1$–$C_4$ alkyl, and
  $R_4$ is linear or branched C9–C22 alkyl, C9–C22 cycloalkyl, C9–C22 aryl or C9–C22 aralkyl and
  n=0 or 1.

The invention is also directed to a method of producing the phosphonate composition having flame retardant properties.

32 Claims, No Drawings

FLAME RETARDANT PHOSPHONATE ADDITIVES FOR THERMOPLASTICS

This invention claims priority from U.S. Patent Application Ser. No. 60/491,914 filed on Aug. 1, 2003.

FIELD OF THE INVENTION

This invention relates to alkyl, cycloalkyl, aryl or aralkyl phosphonates, to specific phosphonates, and, to the use of such phosphonates as, or in connection with flame-retardants in thermoplastics.

BACKGROUND OF THE INVENTION

Flame retardants are incorporated into many products for safety in efforts to control the spread of fire through the product. Flame retardants can, for example, act by causing rapid extinguishing of flames, or by making the product difficult to set afire. While flame retardants have conventionally been used to treat fabrics, soft furnishings, etc. and have been incorporated into foams, paints, and resins such as epoxy resins, many other applications are now being actively pursued, especially within the electronic, automotive, aerospace and construction industries.

Although useful in providing flame retardant properties in thermoplastics, known phosphonate flame retardant additives have disadvantages which limit their use. The present invention provides a phosphonate flame retardant additive which avoids the disadvantages of the known phosphonate flame retardant additives to provide useful compositions.

One disadvantage of the known phosphonate flame retardant additives is that the known flame retardant additives impart a variety of performance problems and other deficiencies to the thermoplastic composition. These problems can limit or eliminate their usefulness with some thermoplastics and in particular, polyolefins. Off-gassing and liquid bleed out in particular have been found in these thermoplastic systems and these disadvantages are believed to have been caused by phosphonate salt/synergist interactions.

Many of the conventional flame retardant additives have been found to have a tendency to migrate and/or volatilize from the thermoplastics over time. The migration of the flame retardant additive causes the object to eventually lose its flame retardant properties. Yet another disadvantage of known phosphonate flame retardants additives are their hygroscopic properties, which will cause thermoplastic objects incorporating these additives to absorb moisture or water over time. Furthermore the known phosphonate flame retardant additives have poor thermal stability. The additives are known to decompose at various thermoplastic processing temperatures, and particularly during the thermoplastic extrusion process.

The present invention seeks to overcome the disadvantages of conventional additives by providing a more stable phosphonate flame retardant additive.

SUMMARY OF THE INVENTION

The invention is directed to a phosphonate composition having flame retardant properties. The phosphonate composition of the invention has the general formula:

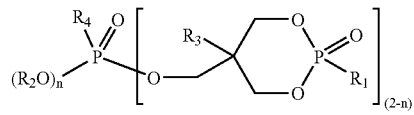

wherein
$R_1$ and $R_2$ are independently $C_1$–$C_4$ alkyl,
$R_3$ is H or $C_1$–$C_4$ alkyl, and
$R_4$ is linear or branched C9–C22 alkyl, C9–C22 cycloalkyl, C9–C22 aryl or C9–C22 aralkyl and
n=0 or 1.
Preferably $R_4$ is a C10–C18 alkyl or C10–C12 cycloalkyl.

The invention is also directed to a method of producing a phosphonate composition having flame retardant properties, in particular flame retardant phosphonates of the general formula;

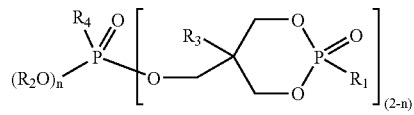

wherein
$R_1$ and $R_2$ are independently $C_1$–$C_4$ alkyl,
$R_3$ is H or $C_1$–$C_4$ alkyl, and
$R_4$ is linear or branched C9–C22 alkyl, C9–C22 cycloalkyl, C9–C22 aryl or C9–C22 aralkyl and
n=0 or 1.
said method comprises the steps of
(1) first reacting trimethylolalkane of general formula:

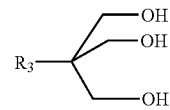

with phosphite of the general formula $P(OR)_3$, wherein R is alkyl, aryl or aralkyl, in a molar ratio sufficient to produce cyclic phosphite of the general formula:

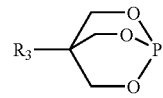

and
(2) reacting the cyclic phosphite with a phosphonate of general formula:

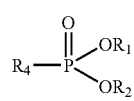

in a molar ratio sufficient to produce the flame retardant phosphonates of the invention.

DETAILED DESCRIPTION OF INVENTION AND PREFERRED EMBODIMENTS

A first subject of the invention is a phosphonate composition having flame retardant properties. There are many phosphonate compounds useful for the present invention. In general these are phosphonate compounds having the following formula:

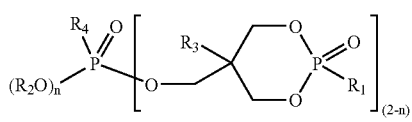

wherein $R_1$ and $R_2$ are independently $C_1$–$C_4$ alkyl, $R_3$ is H or $C_1$–$C_4$ alkyl, and $R_4$ is linear or branched C9–C22 alkyl, C9–C22 cycloalkyl, C9–C22 aryl or C9–C22 aralkyl and n=0 or 1.

Preferably $R_4$ is a C10–C18 alkyl or C10–C12 cycloalkyl.

It is believed that compositions having $R_4$ group with an increased bulkiness of greater than about nine carbon atoms, have improved hydrophobic properties, which are more compatible with thermoplastic material. The improved compatibility provides for a more stable composition, wherein migration of the phosphonate compounds is less likely to occur. Due to the increased hydrophobicity of the additive, a thermoplastic material incorporating a phosphonate in accordance with the invention is less likely to absorb moisture. Furthermore, longer chain phosphonate compounds tend to be more thermally stable. Accordingly phosphonate compositions in accordance with the invention have improved stability properties over conventional phosphonate compounds.

Compounds in accordance with the invention may be prepared by first reacting trimethylolalkane of a general formula (I), for example:

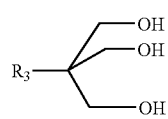

with phosphite of the general formula $P(OR)_3$, wherein R is alkyl, aryl or aralkyl, in a molar ratio sufficient to produce cyclic phosphite of a general formula (II).

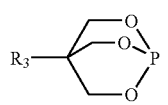

The reaction preferably occurs at temperatures of from about 50° C. to about 200° C.

The reaction can be performed in the presence or absence of a transesterification catalyst.

The process of this invention is conducted for a period of time sufficient to produce the desired compound in adequate yield. Reaction times are influenced to a significant degree by the reaction temperature; the concentration and choice of reactants; the presence of a catalyst; and other factors known to those skilled in the art. In general, reaction times can vary from a few hours to several days or longer.

Examples of trimethylolalkanes include trimethylolmethane, trimethylolethane, trimethylolpropane, and trimethylolbutane. The preferred trimethylolalkane is trimethylolpropane Examples of phosphites are trimethyl phosphite, triethyl phosphite, tripropyl phosphite, tributyl phosphite, trilauryl phosphite, tris-(2-ethylhexyl) phosphite, dimethyl ethyl phosphite, triphenyl phosphite and tritolyl phosphite. The preferred phosphite is trimethyl phosphite.

Examples of transesterification catalysts are methyl acid phosphate, butyl acid phosphate, sulfuric acid and phosphoric acid. The preferred catalyst is methyl acid phosphate.

The cyclic phosphite of general formula (II) is then reacted with phosphonate of a general formula (III):

in a molar ratio sufficient to prepare a flame retardant compound having a general formula (IV):

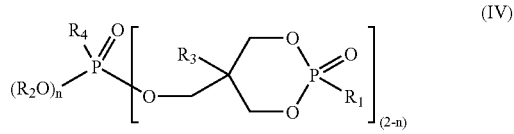

wherein $R_1$ and $R_2$ are independently $C_1$–$C_4$ alkyl, $R_3$ is H or $C_1$–$C_4$ alkyl, and $R_4$ is linear or branched C9–C22 alkyl, C9–C22 cycloalkyl, C9–C22 aryl or C9–C22 aralkyl and n=0 or 1.

The reaction can be performed at temperatures high enough so it can be complete in a reasonable time and low enough so the runaway reaction is avoided. The preferred temperature is from about 180° C. to about 220° C.

The reaction can be carried out in the presence of an alkyl halide as catalyst. The catalyst can be added at the beginning of the reaction or during the reaction, in one portion or several portions or continuously. Examples of alkyl halides are methyl bromide, ethyl bromide, propyl bromide, butyl bromide, octyl bromide, benzyl bromide, ethyl chloride, propyl chloride, butyl chloride, benzyl chloride, methyl iodide, ethyl iodide, propyl iodide and butyl iodide. The preferred alkyl halides are butyl bromide, octyl bromide, methyl iodide, and ethyl iodide.

The reaction can be performed at atmospheric pressure or elevated pressure or under vacuum.

To prevent color formation during the reaction, a color inhibitor can be added. Examples of color inhibitors are N-methylethanol amine, N-diethanol amine, N-triethanol amine, N-ethylethanol amine, N-propylethanol amine. The preferred color inhibitor is N-methylethanol amine.

The process of this invention is conducted for a period of time sufficient to produce the desired compound in adequate yield. Reaction times are influenced to a significant degree by the reaction temperature; the concentration and choice of reactants; the presence of a catalyst; and other factors known to those skilled in the art. In general, reaction times can vary from a few hours to several days or longer.

Illustrative of phosphonates of general formula (III) are dimethyl or diethyl, or dipropyl decylphosphonate, dimethyl or diethyl, or dipropyl laurylphosphonate, dimethyl or diethyl, or dipropyl (4-t-butylcyclohexyl) phosphonate, dimethyl or diethyl, or dipropyl camphylphosphonate, dimethyl or diethyl, or dipropyl (4-t-butylphenylphosphonate, dimethyl or diethyl, or dipropyl (4-t-butylbenzyl) phosphonate, and dimethyl or diethyl, or dipropyl (2-phenylpropyl)phosphonate.

The invention will now be described with reference to a number of specific examples which are to be regarded solely as illustrative of the methods and compositions of this invention and not as restrictive of the scope thereof.

EXAMPLES

In the following examples trimethylol propane phosphite (TMOPP) was used to prepare the flame retardant phosphonates of the invention. Generally the TMOPP was prepared as follows:

Preparation of Trimethylol Propane Phosphite (TMOPP)

In a reaction flask equipped with a mechanical stirrer, nitrogen diptube, addition funnel, heating mantle, thermometer and a short distillation column with takeoff, condenser, and distillate collection vessel, was placed 134 g of trimethylolpropane (TMOP). The reactor was flushed with nitrogen and 124 g of trimethyl phosphite (TMP) was placed in the addition funnel. The reactor was warmed until the TMOP was 80° C. The TMP was then added in one portion. One drop of methyl acid phosphate was added to the reactor as a catalyst. The solution was heated to 90° C., at which point the by-product methanol began to distill. Over the next three hours, the reactor temperature was raised slowly to 140° C. while keeping the top of the column temperature at or below 66° C. Once the reactor temperature reached 140° C., a slow nitrogen sparge was initiated. Distillation of methanol was completed by raising the reactor temperature to 160° C. The reactor residue consisted of 160 g (98.7% yield) of 98% pure by $^{31}$P NMR trimethylol propane phosphite having the following general formula:

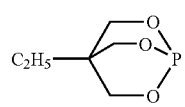

Example 1

Preparation of Flame Retardant Phosphonate A

A flame retardant phosphonate in accordance with the invention and having the following formula was prepared as described in this example.

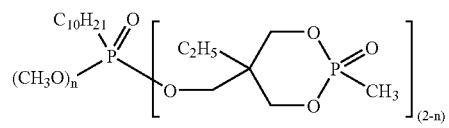

Flame Retardant Phosphonate A

Into a jacketed glass reactor equipped for 1 bar overpressure, with mechanical stirrer, nitrogen blanket, thermometer and vacuum stripping system, was placed 713 g of molten trimethylol propane phosphite (TMOPP) as prepared in above, 550 g of dimethyl decylphosphonate (DMDP), 7.5 g of octyl bromide and 0.5 g of N-methylethanol amine. The mixture was heated to 200° C. under a nitrogen blanket, and then the reactor was sealed. The temperature was held at 200° C. for 11 hours. During the 11 hour time period, the maximum pressure observed was 1000 Torr. Analysis by $^{31}$P NMR showed no TMOPP remaining. The temperature was lowered to 150° C. and the pressure was reduced to 18 Torr to remove volatile by-products. GC analysis showed no DMDP remaining. The reactor residue was a pale yellow viscous liquid that weighed 1240 g (98.2% yield) and displayed the expected $^{31}$P NMR spectrum. The acid number was 5.5. The theoretical % P was 16.2. Analysis for % P by ICP showed 15.8%.

Example 2

Preparation of Flame Retardant Phosphonate B

A flame retardant phosphonate in accordance with the invention and having the following formula was prepared as described in Example 1, except dimethyl camphylphosphonate (542 g) was used instead of dimethyl decylphosphonate.

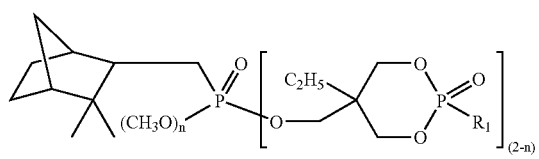

Flame Retardant Phosphonate B

Comparative Examples

The water resistance, thermal stability, and appearance characteristics of the flame retardant phosphonates of the present invention were compared to those of a commercially available flame retardant phosphonate, AMGARD® (Rhodia Inc., Cranbury, N.J.).

Example 3

Water Absorption Comparison

In this example, flame retardant phosphonate A of Example 1 was compared to AMGARDO® CU having the general formula

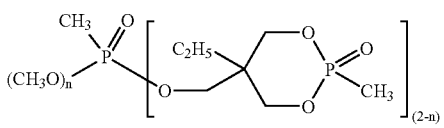

where in n=0 and 1. Two pre-weighed plastics (ABS) coupons (6.5 cm×7.5 cm×0.5 cm) made of
1) 81% wt, ABS (melt index 6 g per 10 min at 230° C. per 3.8 Kg ASTMD 123(8))
2) 16% wt, Bisphenol A bis(diphenyl phosphate),and
3) 3% wt flame retardant phosphonate (either Amgard CU or Phosphonate A)

were immersed in water at 60° C. After 6 hours, the coupons were dried thoroughly and weighed again. Results as shown in Table 1, which indicates that the plastic coupon with flame retardant phosphonate A had improved water resistance.

TABLE 1

| ABS coupon | Water Immersion Test Flame Retardant Phosphonate | % Weight gain |
|---|---|---|
| 1 | Phosphonate A | 3.48% |
| 2 | Amgard CU | 5.64% |

Example 4

Thermal Stability Comparison

The thermal stability of flame retardant phosphonate B of Example 2 was compared to that of AMGARD® (Rhodia, Inc) having the general formula.

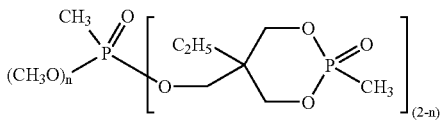

wherein n=0.

The thermal stability of phosphonate B was compared with that of Amgard 1045 using Thermogravimetric Analysis (TgA) (Mettler Toledo). The instrument was preheated to 175° C. and the sample in the range of 5–7 mg was placed in the chamber. The sample was heated and temperature was allowed to increase at a rate of 10° C./min. The sample weight loss was recorded verses temperature. Results, shown in table 2, indicated that the phosphonates of the invention had improved thermal stability compared to the commercially available product.

TABLE 2

Thermal Stability

| Sample | Temperature (° C.) at which sample lost its 10% of original wt |
|---|---|
| Phosphonate FR B | 350 |
| Amgard 1045 | 315 |

The invention claim is:

1. A phosphonate composition having the general formula:

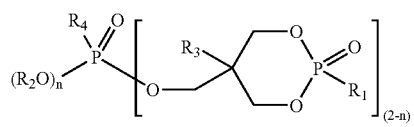

wherein
$R_1$ and $R_2$ are independently $C_1$–$C_4$ alkyl,
$R_3$ is H or $C_1$–$C_4$ alkyl, and
$R_4$ is linear or branched C9–C22 alkyl, C9–C22 cycloalkyl, C9–C22 aryl or C9–C22 aralkyl and
n=0 or 1.

2. The composition of claim 1 wherein R1 and R2 are methyl groups, $R_3$ is ethyl, $R_4$ is substituted or un-substituted C10–C18 alkyl.

3. The composition of claim 2 wherein $R_4$ is C10 or C12 alkyl.

4. The composition of claim 1 wherein $R_1$ and $R_2$ are methyl groups, $R_3$ is ethyl, $R_4$ is substituted or un-substituted C10–C12 cycloalkyl.

5. The composition of claim 4 wherein $R_4$ is 4-t-butylcyclohexyl.

6. The composition of claim 4 wherein $R_4$ is camphyl.

7. A flame retarded thermoplastic resin composition comprising a phosphonate having flame retardant properties, said phosphonate having the general formula

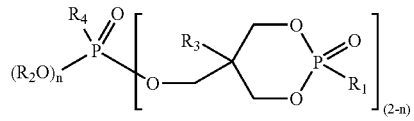

wherein
$R_1$ and $R_2$ are independently $C_1$–$C_4$ alkyl,
$R_3$ is H or $C_1$–$C_4$ alkyl, and
$R_4$ is linear or branched C9–C22 alkyl, C9–C22 cycloalkyl, C9–C22 aryl or C9–C22 aralkyl and
n=0or 1.

8. The composition of claim 7 wherein $R_1$ and $R_2$ are methyl groups, $R_3$ is ethyl, $R_4$ is substituted or un-substituted C10–C18 alkyl.

9. The composition of claim 8 wherein $R_4$ is C10 or C12 alkyl.

10. The composition of claim 7 wherein $R_1$ and $R_2$ are methyl groups, $R_3$ is ethyl, $R_4$ is substituted or un-substituted C10–C12 cycloalkyl.

11. The composition of claim 10 wherein $R_4$ is 4-t-butylcyclohexyl.

12. The composition of claim 10 wherein $R_4$ is camphyl.

13. A method of producing a flame retardant phosphonate composition of the general formula (IV):

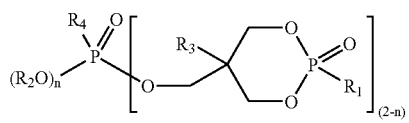

wherein
R$_1$ and R$_2$ are independently C$_1$–C$_4$ alkyl,
R$_3$ is H or C$_1$–C$_4$ alkyl, and
R$_4$ is linear or branched C9–C22 alkyl, C9–C22 cycloalkyl, C9–C22 aryl or C9–C22 aralkyl and
n=0 or 1:
wherein said method comprises the steps of:
1) first reacting trimethylolalkane of general formula (I), wherein R$_3$ is H or C1–C4 alkyl with a phosphite of the general formula P(OR)$_3$, wherein R is alkyl, aryl or aralkyl, in a molar ratio sufficient to produce a cyclic phosphite of general formula (II)

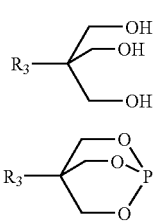

2) second reacting said cyclic phosphite of the general formula (II) with a phosphonate of general formula (III),

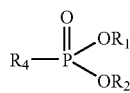

wherein R$_1$ and R$_2$ are independently C$_1$–C$_4$ alkyl and R$_4$ is linear or branched C9–C22 alkyl, C9–C22 cycloalkyl, C9–C22 aryl or C9–C22 aralkyl, in a molar ratio sufficient to produce said flame retardant phosphonate composition of said general formula (IV).

14. The method of claim 13 wherein said step of reacting trimethylolalkane of general formula (I) with said phosphite the general formula P(OR)$_3$ is performed at temperatures of from about 50° C. to about 200° C. in the presence or absence of a transesterification catalyst.

15. The method of claim 14 wherein the said step is performed at temperatures of from about 80° C. to about 160° C.

16. The method of claim 14 wherein the said step is performed in the presence of a transesterification catalyst.

17. The method of claim 16 wherein the acid catalyst is methyl acid phosphate.

18. The method of claim 13 wherein said trimethylolalkane comprises trimethylolpropane.

19. The method of claim 13 wherein said phosphite of the general formula P(OR)$_3$ comprises trimethyl phosphite.

20. The method of claim 13 wherein said phosphite of the general formula P(OR)$_3$ comprises triphenyl phosphite.

21. The method of claim 13 wherein said step of reacting said cyclic phosphite of the general formula (II) with a phosphonate of general formula (III) is performed at temperatures of about 150° C. to about 250° C. in the presence or absence of a alkyl halide catalyst and or a color inhibitor.

22. The method of claim 21 wherein the said step is performed in the presence of an alkyl halide catalyst.

23. The method of claim 22 wherein the alkyl halide catalyst is butyl bromide.

24. The method of claim 22 wherein the alkyl halide catalyst is octyl bromide.

25. The method of claim 22 wherein the alkyl halide catalyst is methyl iodide.

26. The method of claim 21 wherein the said step is performed in the presence of a color inhibitor.

27. The method of claim 26 wherein the color inhibitor is N-methylethanol amine.

28. The method of claim 21 wherein the said step is performed at temperatures of about 180° C. to about 220° C.

29. The method of claim 21 wherein said phosphonate of general formula (III) is dimethyl decylphosphonate.

30. The method of claim 21 wherein said phosphonate of general formula (III) is dimethyl laurylphosphonate.

31. The method of claim 21 wherein said phosphonate of general formula (III) is dimethyl (4-t-butylcyclohexyl) phosphonate.

32. The method of claim 21 wherein said phosphonate of general formula (III) is dimethyl camphylphosphonate.

* * * * *